United States Patent
Borrello et al.

(10) Patent No.: US 11,478,548 B2
(45) Date of Patent: Oct. 25, 2022

(54) MARROW INFILTRATING LYMPHOCYTES (MILS) AS A SOURCE OF T-CELLS FOR CHIMERIC ANTIGEN RECEPTOR (CAR) THERAPY

(71) Applicant: The Johns Hopkins University, Baltimore, MD (US)

(72) Inventors: Ivan M. Borrello, Baltimore, MD (US); Kimberly A. Noonan, Baltimore, MD (US); Drew M. Pardoll, Brookeville, MD (US); Valentina Hoyos Velez, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 625 days.

(21) Appl. No.: 15/742,684

(22) PCT Filed: Jul. 8, 2016

(86) PCT No.: PCT/US2016/041521
§ 371 (c)(1),
(2) Date: Jan. 8, 2018

(87) PCT Pub. No.: WO2017/008019
PCT Pub. Date: Jan. 12, 2017

(65) Prior Publication Data
US 2018/0200367 A1 Jul. 19, 2018

Related U.S. Application Data

(60) Provisional application No. 62/189,928, filed on Jul. 8, 2015.

(51) Int. Cl.
*A61K 39/395* (2006.01)
*C07K 14/725* (2006.01)
*C07K 14/705* (2006.01)
*C07K 14/47* (2006.01)
*A61K 35/17* (2015.01)
*C12N 5/0781* (2010.01)
*C12N 5/0783* (2010.01)

(52) U.S. Cl.
CPC ........ *A61K 39/39558* (2013.01); *A61K 35/17* (2013.01); *C07K 14/4748* (2013.01); *C07K 14/7051* (2013.01); *C07K 14/70521* (2013.01); *C12N 5/0635* (2013.01); *C12N 5/0636* (2013.01); *C07K 2317/622* (2013.01); *C07K 2319/02* (2013.01); *C07K 2319/03* (2013.01); *C12N 2510/00* (2013.01)

(58) Field of Classification Search
CPC .............. A61K 39/39558; A61K 35/17; C07K 14/4748; C07K 14/7051; C07K 14/70521; C07K 2317/622; C07K 2319/02; C07K 2319/03; C12N 5/0635; C12N 5/0636; C12N 2510/00; A61P 31/00; A61P 31/04; A61P 31/10; A61P 31/12; A61P 33/00; A61P 35/00; A61P 37/04; A61P 43/00
See application file for complete search history.

(56) References Cited

U.S. PATENT DOCUMENTS

| 9,272,002 | B2 * | 3/2016 | Powell, Jr. ......... C07K 14/7051 |
| 9,687,510 | B2 * | 6/2017 | Borrello ............... C12N 5/0636 |
| 2011/0223146 | A1 * | 9/2011 | Borrello ............... A61K 31/505 |
| | | | 424/93.71 |
| 2014/0271635 | A1 * | 9/2014 | Brogdon .......... C07K 14/70578 |
| | | | 424/133.1 |
| 2018/0200367 | A1 | 7/2018 | Borrello et al. |

FOREIGN PATENT DOCUMENTS

| MX | 2018/000278 A | 3/2018 | |
| WO | WO-2012079000 A1 * | 6/2012 | .............. A61P 37/02 |
| WO | WO-2013063419 A2 * | 5/2013 | .............. C07K 16/28 |
| WO | WO-2014011988 A2 * | 1/2014 | .............. A61P 37/04 |
| WO | WO-2014/153270 A1 | 9/2014 | |
| WO | WO-2015/092024 A3 | 8/2015 | |
| WO | WO-2016/037054 A1 | 3/2016 | |
| WO | WO-2017/004150 A1 | 1/2017 | |
| WO | WO-2017/008019 A1 | 1/2017 | |

OTHER PUBLICATIONS

Barber et al., J Immunology 180: 72-78 (Year: 2008).*
Gschweng et al., Immunol Rev 257(1): 237-249 (Year: 2014).*
Noonan et al., Cancer Res 65 (5): 2025-2034 (Year: 2005).*
Deaglio et al., J Immunology 160(1): 395-402 (Year: 1998).*
Noonan et al., Cancer Research 65(6): 2026-2034 (Year: 2005).*
Mihara et al., J Immunotherapy 32: 737-743 (Year: 2009).*
International Search Report and Written Opinion for International Application No. PCT/US2016/041521 dated Sep. 22, 2016.
Maus et al.,"Antibody-modified T cells: CARs take the front seat for hematologic malignancies," Blood, 123:2625-2635 (2014).
Noonan et al., "Adoptive transfer of activated marrow-infiltrating lymphocytes induces measurable antitumor immunity in the bone marrow in multiple myeloma," Sci Trans Med, 7(288):288re78 (2015).
Borrello et al., "Marrow-Infiltrating Lymphocytes—Role in Biology and Cancer Therapy," Frontiers in Immunology, 7:1-7 (2016).
Extended European Search Report for EP Application No. 16822042.4 dated Dec. 21, 2018.

* cited by examiner

*Primary Examiner* — Phuong Huynh
(74) *Attorney, Agent, or Firm* — Foley Hoag LLP; Hathaway P. Russell

(57) ABSTRACT

In some embodiments, marrow-infiltrating lymphocytes ("MILs") comprising a chimeric antigen receptor ("CAR") are provided. In some aspects, the embodiments relate to a method for making a recombinant MIL, comprising obtaining bone marrow comprising MILs; and transfecting, transforming, or transducing the MILs with a nucleic acid encoding a chimeric antigen receptor. In some aspects, the embodiments relate to a method for treating a condition in a subject, comprising administering to the subject a MIL comprising a CAR.

8 Claims, No Drawings

MARROW INFILTRATING LYMPHOCYTES (MILS) AS A SOURCE OF T-CELLS FOR CHIMERIC ANTIGEN RECEPTOR (CAR) THERAPY

CROSS-REFERENCE TO RELATED APPLICATIONS

This application is a national stage filing under 35 U.S.C. § 371 of PCT/US16/041521, filed on Jul. 8, 2016, which claims priority to U.S. Provisional Application 62/189,928, filed on Jul. 8, 2015, the contents of each of which are hereby incorporated by reference in their entirety.

BACKGROUND

The large majority of patients with malignancies will die from their disease. One approach to treating these patients is to genetically modify MILs to target antigens expressed on tumor cells through the expression of chimeric antigen receptors ("CARs"). CARs are antigen receptors that are designed to recognize cell surface antigens in a human leukocyte antigen-independent manner. Outside of the successes with CD19-targeted approaches, attempts at using genetically modified cells expressing CARs to treat other malignancies have met with limited success.

SUMMARY

In some embodiments, marrow-infiltrating lymphocytes ("MIL") comprising a chimeric antigen receptor ("CAR") are provided. In some embodiments, the CAR comprises an extracellular domain that can bind a ligand. In some embodiments, the CAR comprises an intracellular domain that can initiate an intracellular signaling cascade (e.g., in the MIL).

In some embodiments, methods for treating a condition in a subject, comprising administering to the subject a MIL comprising a CAR are provided. In some embodiments, the method comprises administering to the subject a composition comprising a population of MILs, wherein each MIL of the population of MILs comprises a CAR.

In some embodiments, methods for making a recombinant MIL, comprising obtaining bone marrow comprising MILs; and transfecting, transforming, or transducing the MILs with a nucleic acid encoding a chimeric antigen receptor are provided. The bone marrow may be obtained from a subject, such as a subject with a neoplasm. The subject may be a human or a mouse.

DETAILED DESCRIPTION

In some embodiments, provided herein are compositions and methods for treating cancer including but not limited to hematologic malignancies and solid tumors. Aspects relate to, but are not limited to, a strategy of adoptive cell transfer of marrow-infiltrating lymphocytes (MILs) transduced to express a chimeric antigen receptor (CAR). CARs are molecules that combine antibody-based specificity for a desired antigen (e.g., tumor antigen) with a MIL receptor-activating intracellular domain to generate a chimeric protein that exhibits a specific anti-tumor cellular immune activity.

In some embodiments, the use of MILs genetically modified to stably express a desired CAR are provided. MILs expressing a CAR are referred to herein as CAR-MILs or CAR-modified MILs. In some embodiments, the cell can be genetically modified to stably express an antibody binding domain on its surface, conferring novel antigen specificity that is MHC independent. In some embodiments, the MIL is genetically modified to stably express a CAR that combines an antigen recognition domain of a specific antibody with an intracellular domain of the CD3ζ chain or FcγRI protein into a single chimeric protein.

In some embodiments, the CAR comprises an extracellular domain having an antigen recognition domain, a transmembrane domain, and a cytoplasmic domain. In some embodiments, the transmembrane domain that naturally is associated with one of the domains in the CAR is used. In some embodiments, the transmembrane domain can be selected or modified by amino acid substitution to avoid binding of such domains to the transmembrane domains of the same or different surface membrane proteins to minimize interactions with other members of the receptor complex. For example, the transmembrane domain may be a CD8α hinge domain.

With respect to the cytoplasmic domain, a CAR, for example, can be designed to comprise the CD28 and/or 4-1BB signaling domain by itself or be combined with any other desired cytoplasmic domain(s) useful in the context of the CAR. In some embodiments, the cytoplasmic domain of the CAR can be designed to further comprise the signaling domain of CD3ζ. For example, the cytoplasmic domain of the CAR can include but is not limited to CD3ζ, 4-1BB, and CD28 signaling modules, and combinations thereof. Accordingly, the embodiments provides CAR-MILs and methods of their use for adoptive therapy.

In some embodiments, the CAR-MILs can be generated by introducing a lentiviral vector comprising a desired CAR (e.g., a CAR comprising anti-CD19, transmembrane domain, and human 4-1BB) into the cells. The CAR-MILs are, for example, able to replicate in vivo resulting in long-term persistence that can lead to sustained tumor control.

In some embodiments, administering a genetically-modified MIL expressing a CAR for the treatment of a patient having a neoplasm using an infusion of CAR-MILs are provided. In some embodiments, autologous infusions are used in the treatment. Autologous MILs are collected from a patient in need of treatment and are activated and expanded using methods described herein and known in the art and then infused back into the patient.

In some embodiments, MILs expressing an anti-CD19 CAR including both CD3ζ and the 4-1BB costimulatory domain are used. In some instances, the CAR MILs infused into a patient can eliminate leukemia cells in vivo in patients. However, the embodiments are not limited to MILs that target CD19 or signal through CD3ζ and/or 4-1BB mediated pathways. For example, the embodiments include any antigen-binding moiety fused with one or more intracellular domains selected from the group consisting of a CD137 (4-1BB) signaling domain, a CD28 signaling domain, a CD3ζ signal domain, and any combination thereof.

Definitions

The articles "a" and "an" are used herein to refer to one or to more than one (i.e., to at least one) of the grammatical object of the article. By way of example, "an element" means one element or more than one element.

As used in this document, terms "comprise," "have," "has," and "include" and their conjugates, as used herein, mean "including but not limited to." While various compositions, and methods are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

"Activation", as used herein, refers to the state of a MIL that has been sufficiently stimulated to induce detectable cellular proliferation. Activation can also be associated with induced cytokine production, and detectable effector functions. The term "activated MILs" refers to, among other things, MILs that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies may exist in a variety of forms including, for example, polyclonal antibodies, monoclonal antibodies, Fv, Fab and F(ab)2, as well as single chain antibodies and humanized antibodies.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the embodiments include, but are not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect that can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies to prevent the occurrence of tumor in the first place.

The term "auto-antigen" means any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a MIL, thereby providing a signal which, in addition to the primary signal provided by, for instance, binding of a TCR/CD3 complex with an MHC molecule loaded with peptide, mediates a MIL response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a MIL, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a MIL that specifically binds with a co-stimulatory ligand, thereby mediating a co-stimulatory response by the MIL, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to MIL proliferation and/or upregulation or downregulation of key molecules.

A "disease" is a state of health of a subject wherein the subject cannot maintain homeostasis, and wherein if the disease is not ameliorated then the animal's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, the following abbreviations for the commonly occurring nucleic acid bases are used. "A" refers to adenosine, "C" refers to cytosine, "G" refers to guanosine, "T" refers to thymidine, and "U" refers to uridine.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "marrow infiltrating lymphocyte" ("MIL") as used herein refers to a lymphocyte derived from the bone marrow. Marrow infiltrating lymphocytes ("MILs") have many distinguishable differences from peripheral blood lymphocytes as well as tumor infiltrating lymphocytes ("TILs"). The bone marrow ("BM") microenvironment is a special immunologic niche due to the richness of antigen presenting cells ("APC"). The presence of these antigen presenting cells allows for the processing and presenting of antigen to sustain the higher levels of central memory cells that are found in the bone marrow compartment. (Li J M et al J Immunol. 2009 Dec. 15; 183(12):7799-809). These MILs express memory markers such as CD45RO+ and CD62L+ and there are more memory MILs than memory cells found in the PBL. (Noonan K et al Clin Cancer Res. 2012 Mar. 1; 18(5):1426-34). Furthermore, MILs are not just the "TILs" of hematologic malignancies because of their ability to continuously prime memory cells to antigen (Beckhove P et al J Clin Invest. 2004 Jul. 1; 114(1): 67-76; Castiglioni P et al 6 J Immunol 2008; 180:4956-4964). MILs also express more CXCR4 than their PBL counterparts due to the cognate antigen stromal derived factor type 1 ("SDF1") that is expressed in great amounts in the bone marrow stroma (Noonan K et al Cancer Res. 2005 Mar. 1; 65(5):2026-34). The expression of 41BB is also increased in MILs compared to PBLs, likely due to the hypoxic nature of the BM micro-environment. Further, MILs can be harvested and expanded from all patients, in contrast with TILs (Noonan, K et al Sci Transl Med. 2015 May 20; 7(288): 288ra78). TILs are found in only about 50% of patients, and only about 25% of patients comprise expandable TILs. In contrast to peripheral blood lymphocytes (PBLs), MILs possess a broad endogenous antigenic repertoire which account for their intrinsic tumor specificity—a feature which is completely absent in PBLs (Noonan et al Clin Cancer Res).

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a MTh that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a MIL, thereby mediating a primary response by the MIL, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Examples of subjects include humans, dogs, cats, mice, rats, and transgenic species thereof.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor, or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

DESCRIPTION

The present disclosure provides compositions and methods for treating cancer among other diseases. The cancer may be a hematological malignancy, a solid tumor, a primary or a metastasizing tumor. The cancer may be a hematological malignancy, such as Chronic Lymphocytic Leukemia ("CLL"). Other diseases treatable using the compositions and methods described and provided for herein include viral, bacterial, and parasitic infections as well as autoimmune diseases.

In some embodiments, the cell (i.e., MIL) engineered to express a CAR wherein the CAR-MIL exhibits an antitumor property is provided. The CAR can, for example, be engineered to comprise an extracellular domain having an antigen-binding domain fused to an intracellular signaling domain of the MIL antigen receptor complex chain (e.g., CD3ζ). The CAR, for example, when expressed in a MIL, is able to redirect antigen recognition based on the antigen-binding specificity. In some embodiments, the antigen is CD19 because this antigen is expressed on malignant B cells. However, the embodiments are not limited to targeting CD19. Rather, the embodiments include any antigen-binding moiety that when bound to its cognate antigen, affects a tumor cell so that the tumor cell fails to grow, is prompted to die, or otherwise is affected so that the tumor burden in a patient is diminished or eliminated. The antigen-binding moiety may be fused with an intracellular domain from one or more of a costimulatory molecule and a ζ chain. In some embodiments, the antigen-binding moiety is fused with one or more intracellular domains selected from the group of a CD137 (4-1BB) signaling domain, a CD28 signaling domain, a CD3ζ signal domain, and any combination thereof. The antigen-binding moiety may also be fused with an intracellular domain such as CD134 (OX40).

In some embodiments, the CAR comprises a CD137 (4-1BB) signaling domain. Without being bound to any particular theory, this is because the embodiments are partly based on the discovery that CAR-mediated T-cell responses can be further enhanced with the addition of costimulatory domains.

I. CHIMERIC ANTIGEN RECEPTORS

Provided herein are chimeric antigen receptors (CARs) comprising an extracellular and intracellular domain. The extracellular domain comprises a target-specific binding element otherwise referred to as an antigen-binding moiety. The intracellular domain or otherwise the cytoplasmic domain may comprise a costimulatory signaling region and/or a portion of a ζ chain. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

A spacer domain may be incorporated between the extracellular domain and the transmembrane domain of the CAR or between the cytoplasmic domain and the transmembrane domain of the CAR. As used herein, the term "spacer domain" generally means a stretch of amino acids that functions to link the transmembrane domain to either the extracellular domain or the cytoplasmic domain in the polypeptide chain. A spacer domain may comprise up to 300 amino acids, preferably 2 to 100 amino acids, such as 25 to 50 amino acids.

II. EXTRACELLULAR DOMAINS

In some embodiments, the CAR comprises a target-specific binding element otherwise referred to as an antigen-binding moiety. The choice of moiety depends upon the type and number of ligands that define the surface of a target cell. For example, the antigen-binding domain may be chosen to recognize a ligand that acts as a cell surface marker on target cells associated with a particular disease state. Thus, examples of cell surface markers that may act as ligands for the antigen-binding domain in a CAR include those associated with viral, bacterial, and parasitic infections, autoimmune disease, and cancer cells. For example, the ligand may be the protein of a bacterium, virus, or parasite. Similarly, the ligand may be a protein that is upregulated on the surface of a cancer cell.

In some embodiments, a CAR can be engineered to target a tumor antigen of interest by way of engineering a desired antigen-binding moiety that specifically binds to an antigen on a tumor cell. As used herein, "tumor antigen" or "hyperproliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen-binding moiety will depend on the particular type of cancer to be treated. Tumor antigens are well known in the art and include, for example, a glioma-associated antigen, carcinoembryonic antigen (CEA), β-human chorionic gonadotropin, alpha-fetoprotein (AFP), lectin-reactive AFP, thyroglobulin, RAGE-1, MN-CA IX, human telomerase reverse transcriptase, RU1, RU2 (AS), intestinal carboxyl esterase, mutant hsp70-2, M-CSF, prostase, prostate-specific antigen (PSA), PAP, NY-ESO-1, LAGE-1a, p53, prostein, PSMA, Her2/neu, survivin, telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, and mesothelin.

In some embodiments, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase, and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma, the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (e.g., CEA, HER-2, CD19, CD20, idiotype) have been used as targets for passive immunotherapy with monoclonal antibodies with limited success.

The type of tumor antigen referred to may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a some embodiments, the antigen-binding moiety portion of the CAR targets an antigen that includes but is not limited to CD19, CD20, CD22, ROR1, Mesothelin, CD33/IL3Ra, c-Met, PSMA, Glycolipid F77, EGFRvIII, GD-2, MY-ESO-1 TCR, MAGE A3 TCR, and the like.

Depending on the desired antigen to be targeted, a CAR can be engineered to include the appropriate antigen bind moiety that is specific to the desired antigen target. For example, if CD19 is the desired antigen that is to be targeted, an antibody for CD19 can be used as the antigen bind moiety for incorporation into the CAR. Thus, in some embodiments, the antigen-binding moiety portion of the CAR targets CD19.

The extracellular domain of a CAR may comprise, for example, a single-chain variable fragment ("scFv") that binds to any one of the targets described herein.

The extracellular domain can be any antigen-binding polypeptide, a wide variety of which are known in the art. In some instances, the antigen-binding domain is a single chain Fv ("scFv"). Other antibody based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use. In some instances, T-cell receptor (TCR) based recognition domains such as single chain TCR (scTv, single chain two-domain TCR containing v vβ) are also suitable for use.

Other extracellular domains known in the art may also be used in embodiments (see, e.g., PCT Patent Application Publication No. WO 2014/127261; U.S. Pat. No. 8,975,071, hereby incorporated by reference).

III. TRANSMEMBRANE DOMAINS

With respect to the transmembrane domain, the CAR can be designed to comprise a transmembrane domain that is fused to the extracellular domain of the CAR. In some embodiments, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural source or the transmembrane domain may be designed (e.g., from a stretch of 18 to 30 hydrophobic amino acids, such as alanine, valine, leucine, and isoleucine, which form an α-helix). Where the source is natural, the domain may be derived from any membrane-bound or transmembrane protein. Transmembrane regions of particular use may be derived from (i.e., comprise at least the transmembrane region(s) of) the α, β, or ζ chain of the T-cell receptor, CD28, CD3 epsilon, CD45, CD4, CD5, CD8, CD9, CD16, CD22, CD33, CD37, CD64, CD80, CD86, CD134, CD137, or CD154. Alternatively the transmembrane domain may be designed, in which case it will comprise predominantly hydrophobic residues such as leucine and valine. For a designed transmembrane domain, phenylalanine, tryptophan, and/or tyrosine may be found near the membrane/water interface. Optionally, a short oligo- or polypeptide linker between 2 and 10 amino acids in length may link the transmembrane domain and the cytoplasmic signaling domain of the CAR. A glycine-serine spacer provides a particularly suitable linker.

IV. INTRACELLULAR DOMAIN

The cytoplasmic domain or otherwise the intracellular signaling domain of the CAR is responsible for activation of at least one of the normal effector functions of a MIL. The term "effector function" refers to a specialized function of a cell. An effector function of a MIL, for example, may be cytolytic activity or helper activity including the secretion of cytokines. Thus the term "intracellular signaling domain" refers to the portion of a protein which transduces the effector function signal and directs the cell to perform a specialized function. While an entire intracellular signaling domain can be employed, in many cases it is not necessary to use the entire intracellular domain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Some non-limiting examples of intracellular signaling domains for use in the CAR include the cytoplasmic sequences of the T-cell receptor (TCR) and co-receptors that act in concert to initiate signal transduction following antigen receptor engagement, as well as any derivative or variant of these sequences and any synthetic sequence that has the same functional capability.

Signals generated through the TCR alone are insufficient for full activation of a lymphocyte, and a secondary or co-stimulatory signal is also required. Thus, MIL activation is mediated by two distinct classes of cytoplasmic signaling: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs that are known as immunoreceptor tyrosine-based activation motifs or ITAMs.

Examples of ITAM containing primary cytoplasmic signaling sequences that can be used include, but are not limited to, those derived from TCRζ, FcR gamma, FcR beta, CD3γ, CD3δ, CD3ε, CD5, CD22, CD79a, CD79b, and CD66d. In some embodiments, the cytoplasmic signaling molecule of the CAR comprises a cytoplasmic signaling sequence derived from CD3ζ.

In some embodiments, the cytoplasmic domain of the CAR can be designed to comprise the CD3ζ signaling domain by itself or combined with any other desired cytoplasmic domain(s) useful in the context of a CAR. For example, the cytoplasmic domain of the CAR may comprise a portion of a CD3ζ chain and a costimulatory signaling region. The costimulatory signaling region refers to a portion of the CAR comprising the intracellular domain of a costimulatory molecule. In some embodiments, the costimulatory molecule is a cell surface molecule other than an antigen receptor or their ligands that is required for an efficient response by lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and the like. Thus, while some embodiments may be exemplified with 4-1BB as the co-stimulatory signaling element, other costimulatory elements can also be used.

The cytoplasmic signaling sequences within the cytoplasmic signaling portion of a CAR may be linked to each other in a random or specified order. Optionally, short oligo- or polypeptide linkers, preferably between 2 and 10 amino acids in length may form the linkage. A glycine-serine spacer provides a particularly suitable linker.

In some embodiments, the cytoplasmic domain is designed to comprise the signaling domain of CD3ζ and the signaling domain of CD28. In some embodiments, the cytoplasmic domain is designed to comprise the signaling domain of CD3ζ and the signaling domain of 4-1BB. In some embodiments, the cytoplasmic domain is designed to comprise the signaling domain of CD3ζ and the signaling domain of CD28 and 4-1BB.

In some embodiments, the cytoplasmic domain in the CAR is designed to comprise the signaling domain of 4-1BB and the signaling domain of CD3ζ.

V. VECTORS

The expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The expression constructs may also be used for nucleic acid immunization and gene therapy, using standard gene delivery protocols. Methods for gene delivery are known in the art (see, e.g., U.S. Pat. Nos. 5,399,346, 5,580,859, 5,589,466, hereby incorporated by reference). In some embodiments, the embodiments provide a gene therapy vector. The nucleic acid sequence may also be inserted using gene editing techniques such as, but not limited to, CRISPR.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

An expression vector may be provided to a cell in the form of a viral vector. Viral vector technology is well known in the art and is described, for example, in Green & Sambrook (*Molecular Cloning: A Laboratory Manual*, (4th ed., 2012)), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. In some embodiments, adenovirus vectors are used. In some embodiments, lentivirus vectors are used.

Additional regulatory elements (e.g., promoters and enhancers) regulate the frequency of transcriptional initiation. Typically, these are located 30-100,000 bp upstream of the start site, although a number of promoters have recently been shown to contain functional elements downstream of the start site as well. The spacing between promoter elements is frequently flexible, so that promoter function is preserved when elements are inverted or moved relative to one another. In the thymidine kinase (tk) promoter, the spacing between promoter elements can be increased by 50 bp apart before activity begins to decline. Depending on the promoter, individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoters are not limited to constitutive promoters.

Inducible promoters can also be used. The use of an inducible promoter provides a molecular switch capable of turning on expression of the polynucleotide sequence that is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). In some embodiments, the reporter gene is mCherry.

Methods of introducing and expressing genes into a cell are well known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art (see, e.g., Green & Sambrook, *Molecular Cloning: A Laboratory Manual*, (4th ed., 2012)).

Biological methods for introducing a polynucleotide of interest into a host cell include the use of DNA and RNA vectors. Viral vectors, and especially retroviral vectors, have become a widely used method for inserting genes into mammalian cells. Other viral vectors can be derived from lentivirus, poxviruses, herpes simplex virus I, adenoviruses, adeno-associated viruses, and the like (see, e.g., U.S. Pat. Nos. 5,350,674 and 5,585,362).

Chemical means for introducing a nucleic acid into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo, or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained, or complexed with a micelle, or otherwise associated with a lipid. Lipid, lipid/DNA, or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape.

VI. MARROW INFILTRATING LYMPHOCYTES

Prior to expansion and genetic modification of the MILs, a source of MILs is obtained from a subject. In patients with any of a number of types of cancer, including hematologic malignancies and solid tumors, T cells can easily be obtained from the bone marrow microenvironment with heightened tumor specificity as compared to peripheral blood (see, e.g., U.S. Patent Application Publication No. U.S. 2011/0223146, hereby incorporated by reference). By comparing T cells obtained from these two different compartments from a subject having a hematological malignancy, oligoclonal restriction of marrow infiltrating lymphocytes (MILs) obtained from marrow aspirates is observed. Methods, such as those including anti-CD3/CD28 antibody-conjugated magnetic beads, may be used to activate and expand the bone marrow cells in vitro to generate activated MILs. The activated MILs show a greater expansion and enhanced tumor activity as compared to peripheral blood lymphocytes in all patients examined. These findings suggest that: 1) the marrow is a reservoir of tumor-specific T cells; 2) MILs can be activated and expanded in all patients studied (as compared to the limited numbers observed in metastatic melanoma); 3) these cells traffic to the bone marrow upon infusion; 4) persist for up to 200 days following adoptive transfer in NOD/SCID mice; and that 5) activated MILs are capable of eradicating pre-established disease and targeting myeloma stem cell precursors thus implying a broad antigenic recognition.

The T-cells, which represent a minority of the total bone marrow cell population may be expanded in the presence of almost complete bone marrow. To assure maximal tumor-T cell contact, the aspirated bone marrow may be fractionated on a Lymphocyte Separation Medium density gradient and cells may be collected almost to the level of the red cell pellet. This separation method removes substantially only the red blood cells and the neutrophils, providing nearly complete bone marrow, and results in the collection of both T cells as well as tumor cells. T-cells may be expanded without a T-cell specific separation step, and without a tumor cell separation step. Cell type specific separation steps include, for example, cell labeling using antibodies or other cell-type specific detectable labels, and sorting using fluorescence activated cell sorting (FACS). In some embodiments, the methods can be practiced without such labeling and cell sorting methods.

For activation with beads, bead-T cell contact is preferably maximized during the first 24-48 hours of culture. As the T-cells represent only a minority of the total cells in the population, contact of the T-cells with the antibody coated beads is promoted by the use of a sufficient number of beads to cells, in the range of about 1:1 to about 5:1 beads to cells, preferably about 2:1 to 4:1 beads to cells, more preferably about 2.5:1 to 3.5:1 beads to cells. These ratios are applicable for the disclosed beads, and a change in the size of the beads and/or the density of antibodies on the beads can alter the bead:cell ratio.

In some embodiments, a device may be utilized for culturing the cells, providing a smooth, rigid, rounded bottom surface to promote collection of the cells and beads by gravity in close proximity (see, e.g., U.S. Patent Application Publication No. U.S. 2011/0223146, hereby incorporated by reference). The device includes an enclosed cell container that rests on a support. During at least the first 3 days of culture in the presence of the beads, the container is preferably stationary (i.e., no rocking or rotation) to further promote contact between the beads and the cells. These steps and conditions are preferable for maximizing the expansion of tumor-specific MILs using beads, to allow for the production of sufficient cells to be therapeutically useful. Further, these culture conditions promote growth of the T cells without promoting growth of the tumor cells.

Several attributes of MILs make them suitable candidates for immunotherapy. Specifically, under the conditions described herein, they expand more rapidly upon stimulation than PBLs and often maintain a skewed T-cell repertoire upon activation, possibly suggesting augmented tumor specificity. Whereas the unactivated MILs show profound hyporesponsiveness toward autologous tumor, the ability to activate and expand T cells and markedly enhance their tumor reactivity argues against deletional tolerance as a presumptive mechanism mediating T-cell unresponsiveness in this setting. Furthermore, activated MILs show tumor specificity with little cross-reactivity towards nonmalignant hematopoietic elements, have a higher expression of CXCR-4, and possess a greater responsiveness to SDF-I, suggesting an increased migratory ability of MILs to the bone marrow. Taken together, these findings show the ability to activate and expand marrow-infiltrating T cells with a memory/effector phenotype that seem to target the broad range of tumor antigens present on both mature terminally differentiated plasma cells as well as their precursors and possess chemokine receptors that would seem to facilitate trafficking to the bone marrow compartment—features that would be necessary for maximizing antitumor immunity of adoptive immunotherapy.

Activation and expansion of MILs was based on two previously reported phenomena: the enhanced tumor specificity of tumor-infiltrating lymphocytes (Rosenberg et al. Science 1986; 233:1318) and the demonstration of tumor-reactive T cells in the bone marrow of patients with melanoma (Letsch et al. Cancer Res 2003; 63:5582-6), breast cancer (Feuerer et al. Nat Med 2001; 7:452), and multiple myeloma—a disease in which the bone marrow also represents the tumor microenvironment (Dhodapkar et al. Proc Natl Acad Sci USA 2002; 99:13009).

The ability to activate and expand MILs as a means of overcoming their unresponsiveness and significantly increasing their tumor specificity compared with activated PBLs is provided herein. The presence of tumor in the bone marrow microenvironment may play a critical role in preserving the antigen specificity of activated MILs. Several hypotheses may explain the increased reactivity of activated MILs over activated PBLs. Without being bound by mechanism, it is suggested that the persistence of antigen in the bone marrow may be essential for the maintenance of a memory response. Anti-CD3/CD28 antibody-coated bead activation may be reversing tolerance in the bone marrow T-cell population. Similarly, plate bound and/or soluble CD3 and/or CD28 may be used for activation. The means of activating MILs, however, is not particularly limiting, and any suitable method of activation may be used in various embodiments. As demonstrated herein, the tumor specificity of activated MILs was dependent on the presence of antigen during T-cell activation. Further, the bone marrow is a functional lymphoid organ capable of mounting both a primary immune response and a secondary responses via reactive lymphoid follicles in the presence of danger signals (infection, inflammation, autoimmunity, and cancer).

T cells in myeloma patients show considerable skewing of the VB T-cell receptor repertoire. Such skewing suggests either the selective outgrowth of T cells with marked tumor specificity or results from the profound underlying T-cell defects characteristic of patients with a significant tumor burden. In the latter case, a benefit of polyclonal stimulation of PBLs with the anti-CD3/CD28 antibody-conjugated magnetic beads is the ability to restore a normal T-cell repertoire and thus correct any underlying T-cell defects. In contrast, if the oligoclonal expression of specific VB families reflects the presence of T cells with tumor specificity, activation and expansion of this pool of T cells with maintained antitumor activity and T-cell receptor repertoire skewing may be preferable. As demonstrated herein, PBLs normalized their VB T-cell repertoire upon activation and expansion with anti-CD3/CD28 antibody-conjugated magnetic beads, whereas MILs maintained the VB restriction. Considering the enhanced tumor-specific response of activated MILs, their skewed T-cell repertoire may be suggestive of greater tumor recognition. Without being bound by mechanism, it may be important to conserve and possibly increase the degree of VB skewing during T-cell expansion.

The activation and expansion of MILs with anti-CD3/CD28 antibody-conjugated magnetic beads generates potent antitumor activity and the persistence of antigen during this expansion may be of significant importance in maintaining (and augmenting) the tumor specificity. Dhodapkar et al. (2002) have also studied the role of MILs in myeloma patients. Similar to our findings, freshly isolated MILs or PBLs showed no activity upon stimulation with autologous tumor or tumor peptides. However, whereas that study saw no significant differences between T cells obtained from the peripheral blood and the marrow compartment in the enzyme-linked immunospot assay following 12 to 16 days of incubation with tumor-pulsed dendritic cells, a 10-fold greater antitumor response of activated MILs over activated PBLs was observed in our system in all assays examined. These discrepant results may be related to potency of anti-CD3/CD28 bead stimulation as compared with dendritic cell activation of MILs. Without being bound by mechanism, what seems to be an increase in frequency of tumor-reactive T cells in the activated and expanded MILs cultures may reflect the breaking of tolerance and restoration of function of tumor-reactive T cells. Furthermore, stimulation of MILs within the bone marrow microenvironment is another important factor that may explain these results.

Enrichment of a MIL population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads.

In some embodiments, it may be desirable to use lower concentrations of cells. By significantly diluting the mixture of MILs and surface (e.g., particles such as beads), interactions between the particles and cells is minimized. This selects for cells that express high amounts of desired antigens to be bound to the particles.

Also provided herein is the collection of samples comprising MILs from a subject at a time period prior to when the expanded cells as described herein might be needed. As such, the source of the cells to be expanded can be collected at any time point necessary, and desired cells, such as MILs, isolated and frozen for later use in MIL therapy for any number of diseases or conditions that would benefit from MIL therapy, such as those described herein. In some embodiments a sample comprising MILs is taken from a generally healthy subject. In some embodiments, a sample comprising MILs is taken from a generally healthy subject who is at risk of developing a disease, but who has not yet developed a disease, and the cells of interest are isolated and frozen for later use. In some embodiments, the MILs may be expanded, frozen, and used at a later time. In some embodiments, samples are collected from a patient shortly after diagnosis of a particular disease as described herein but prior to any treatments. In some embodiments, the cells are isolated from a sample comprising MILs from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). In some embodiments, the cells are isolated for a patient and frozen for later use in conjunction with (e.g., before, simultaneously or following) bone marrow or stem cell transplantation, MIL ablative therapy using either chemotherapy agents such as, fludarabine, external-beam radiation therapy (XRT), cyclophosphamide, or antibodies such as OKT3 or CAMPATH. In some embodiments, the cells are isolated prior to and can be frozen for later use for treatment following B-cell ablative therapy such as agents that react with CD20, e.g., Rituxan.

In some embodiments, MILs are obtained from a patient directly following treatment. In this regard, it has been observed that following certain cancer treatments, in particular treatments with drugs that damage the immune system, shortly after treatment during the period when patients would normally be recovering from the treatment, the quality of MILs obtained may be optimal or improved for their ability to expand ex vivo. Likewise, following ex vivo manipulation using the methods described herein, these cells may be in a preferred state for enhanced engraftment and in vivo expansion. Thus, the MILs may be collected during this recovery phase.

Whether prior to or after genetic modification of the MILs to express a desirable CAR, the MILs can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005 (hereby incorporated by reference).

In some embodiments, the MILs are expanded by contact with a surface having attached thereto an agent that stimulates a CD3/TCR complex associated signal and a ligand that stimulates a co-stimulatory molecule on the surface of the MILs. In particular, MIL populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the MILs, a ligand that binds the accessory molecule is used. For example, a population of MILs can be contacted with an anti-CD3 antibody and an anti-CD28 antibody, under conditions appropriate for stimulating proliferation of the MILs. To stimulate proliferation of either CD4+ MILs or CD8+ MILs, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the MIL may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In some embodiments, the agent providing the co-stimulatory signal is bound to a cell surface and the agent providing the primary activation signal is in solution or coupled to a surface. In certain embodiments, both agents can be in solution. In some embodiments, the agents may be in soluble form, and then cross-linked to a surface, such as a cell expressing Fc receptors or an antibody or other binding agent which will bind to the agents. (see generally U.S. Patent Application Publication Nos. 20040101519 and 20060034810, hereby incorporated by reference, especially for artificial antigen presenting cells (aAPCs) that are contemplated for use in activating and expanding MILs).

In some embodiments, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In some embodiments, a 1:1 ratio of each antibody bound to the beads for CD4+ MIL expansion and MTh growth is used. In some embodiments, a ratio of anti CD3:CD28 antibodies bound to the beads is used such that an increase in MIL expansion is observed as compared to the expansion observed using a ratio of 1:1. In some embodiments an increase of from about 1 to about 3 fold is observed as compared to the expansion observed using a ratio of 1:1. In some embodiments, the ratio of CD3:CD28 antibody bound to the beads ranges from 100:1 to 1:100 and all integer values there between. In some embodiments, more anti-CD28 antibody is bound to the particles than anti-CD3 antibody, i.e., the ratio of CD3:CD28 is less than one. In some embodiments, the ratio of anti CD28 antibody to anti CD3 antibody bound to the beads is greater than 2:1. In some embodiments, a 1:100 CD3:CD28 ratio of antibody bound to beads is used. In some embodiments, a 1:75 CD3:CD28 ratio of antibody bound to beads is used. In some embodiments, a 1:50 CD3:CD28 ratio of antibody bound to beads is used. In some embodiments, a 1:30 CD3:CD28 ratio of antibody bound to beads is used. In some embodiments, a 1:10 CD3:CD28 ratio of antibody bound to beads is used. In some embodiments, a 1:3 CD3:CD28 ratio of antibody bound to the beads is used. In some embodiments, a 3:1 CD3:CD28 ratio of antibody bound to the beads is used.

Ratios of particles to cells from 1:500 to 500:1 and any integer values in between may be used to stimulate MILs. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate MILs. The ratio of anti-CD3- and anti-CD28-coupled particles to cell that result in MIL stimulation can vary as noted above, however certain values include, but are not limited to, 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1. In some embodiments, the ratio is at least 1:1 particles per cell. In some embodiments, a ratio of particles to cells of 1:1 or less is used. In some embodiments, a particle:cell ratio is 1:5. In some embodiments, the ratio of particles to cells can be varied depending on the day of stimulation. For example, in some embodiments, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In some embodiments, the ratio of particles to cells is 1:1 on the first day of stimulation and adjusted to 1:5 on the third and fifth days of stimulation. In some embodiments, particles are added on a daily or every other day basis to a final ratio of 1:1 on the first day, and 1:5 on the third and fifth days of stimulation. In some embodiments, the ratio of particles to cells is 2:1 on the first day of stimulation and adjusted to 1:10 on the third and fifth days of stimulation. In some embodiments, particles are added on a daily or every other day basis to a final ratio of 1:1 on the first day, and 1:10 on the third and fifth days of stimulation. One of skill in the art will appreciate that a variety of other ratios may also be used. For example, ratios will vary depending on particle size and on cell size and type.

In some embodiments, the MILs are combined with agent-coated beads, the beads and the cells are subsequently separated, and then the cells are cultured. In some embodiments, prior to culture, the agent-coated beads and cells are not separated but are cultured together. In some embodiments, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the MILs. In some embodiments the cells and beads (for example, DYNABEADS® M-450 CD3/CD28 T paramagnetic beads at a ratio of 1:1) are combined in a buffer, preferably PBS (without divalent cations such as, calcium and magnesium). Those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number can be used. In certain embodiments, it may be desirable to significantly decrease the volume in which particles and cells are mixed together (i.e., increase the concentration of cells), to ensure maximum contact of cells and particles. For example, in some embodiments, a concentration of about 2 billion cells/ml is used. In some embodiments, greater than 100 million cells/ml is used. In some embodiments, a concentration of cells of 10, 15, 20, 25, 30, 35, 40, 45, or 50 million cells/ml is used. In some embodiments, a concentration of cells from 75, 80, 85, 90, 95, or 100 million cells/ml is used. In some embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative cells. Such populations of cells may have therapeutic value and would be desirable to obtain in certain embodiments.

In some embodiments, the mixture may be cultured for several hours (about 3 hours) to about 14 days or any hourly integer value in between. In some embodiments, the mixture may be cultured for 21 days. In some embodiments the beads and the MILs are cultured together for about eight days. In some embodiments, the beads and MILs are cultured together for 2-3 days. Several cycles of stimulation may also be desired such that culture time of MILs can be 60 days or more. Conditions appropriate for MIL culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of MILs. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In addition to CD4 and CD8 markers, other phenotypic markers vary significantly, but in large part, reproducibly during the course of the cell expansion process. Thus, such reproducibility enables the ability to tailor an activated MIL product for specific purposes.

Additionally, methods for preparing tumor infiltrating lymphocytes may be used to prepare MILs. For example, high does IL-2 growth conditions may be used to generate "young" TILs, and these methods are applicable to preparing MILs (see, e.g., U.S. Pat. No. 8,383,099, hereby incorporated by reference).

In some embodiments, the MILs can also be activated and/or expanded under hypoxic conditions. An example of growing the MILs under hypoxic conditions can found, for example, in WO2016037054, which is hereby incorporated by reference in its entirety.

In some embodiments, the method may comprise removing cells in the bone marrow, lymphocytes, and/or marrow infiltrating lymphocytes ("MILs") from the subject; incubating the cells in a hypoxic environment, thereby producing activated MILs; and administering the activated MILs to the subject. The cells can also be activated in the presence of anti-CD3/anti-CD28 antibodies and cytokines as described herein. Cyotkines can also be used to activate the MILs as described herein. A nucleic acid molecule encoding the CAR, such as one of those described herein, can be transfected or infected into a cell before or after the MIL is incubated in a hypoxic environment.

The hypoxic environment may comprise less than about 21% oxygen, such as less than about 20%, 19%, 18%, 17%, 16%, 15%, 14%, 13%, 12%, 11%, 10%, 9%, 8%, 7%, 6%, 5%, 4%, or less than about 3% oxygen. For example, the hypoxic environment may comprise about 0% oxygen to about 20% oxygen, such as about 0% oxygen to about 19% oxygen, about 0% oxygen to about 18% oxygen, about 0% oxygen to about 17% oxygen, about 0% oxygen to about 16% oxygen, about 0% oxygen to about 15% oxygen, about 0% oxygen to about 14% oxygen, about 0% oxygen to about 13% oxygen, about 0% oxygen to about 12% oxygen, about 0% oxygen to about 11% oxygen, about 0% oxygen to about 10% oxygen, about 0% oxygen to about 9% oxygen, about 0% oxygen to about 8% oxygen, about 0% oxygen to about 7% oxygen, about 0% oxygen to about 6% oxygen, about 0% oxygen to about 5% oxygen, about 0% oxygen to about 4% oxygen, or about 0% oxygen to about 3% oxygen. In some embodiments, the hypoxic environment comprises about 1% to about 7% oxygen. In some embodiments, the hypoxic environment is about 1% to about 2% oxygen. In some embodiments, the hypoxic environment is about 0.5% to about 1.5% oxygen. In some embodiments, the hypoxic environment is about 0.5% to about 2% oxygen. The hypoxic environment may comprise about 20%, 19%, 18%, 17%, 16%, 15%, 14%, 13%, 12%, 11%, 10%, 9%, 8%, 7%, 6%, 5%, 4%, 3%, 2%, 1%, or about 0% oxygen. In some embodiments, the hypoxic environment comprises about 7%, 6%, 5%, 4%, 3%, 2%, or 1% oxygen.

Incubating MILs in a hypoxic environment may comprise incubating the MILs, e.g., in tissue culture medium, for at least about 1 hour, such as at least about 12 hours, 18 hours, 24 hours, 30 hours, 36 hours, 42 hours, 48 hours, 60 hours, 3 days, 4 days, 5 days, 6 days, 7 days, 8 days, 9 days, 10 days, 11 days, 12 days, 13 days, or even at least about 14 days. Incubating may comprise incubating the MILs for about 1 hour to about 30 days, such as about 1 day to about 20 days, about 1 day to about 14 days, or about 1 day to about 12 days. In some embodiments, incubating MILs in a hypoxic environment comprises incubating the MILs in a hypoxic environment for about 2 days to about 5 days. The method may comprise incubating MILs in a hypoxic environment for about 1 day, 2 days, 3 days, 4 days, 5 days, 6 days, 7 days, 8 day, 9 days, 10 days, 11 days, 12 days, 13 days, or 14 days. In some embodiments, the method comprises incubating the MILs in a hypoxic environment for about 3 days. In some embodiments, the method comprises incubating the MILs in a hypoxic environment for about 2 days to about 4 days. In some embodiments, the method comprises incubating the MILs in a hypoxic environment for about 3 days to about 4 days.

In some embodiments, the method further comprises incubating the MILs in a normoxic environment, e.g., after incubating the MILs in a hypoxic environment.

The normoxic environment may comprise at least about 21% oxygen. The normoxic environment may comprise about 5% oxygen to about 30% oxygen, such as about 10% oxygen to about 30% oxygen, about 15% oxygen to about 25% oxygen, about 18% oxygen to about 24% oxygen, about 19% oxygen to about 23% oxygen, or about 20% oxygen to about 22% oxygen. In some embodiments, the normoxic environment comprises about 21% oxygen.

Incubating MILs in a normoxic environment may comprise incubating the MILs, e.g., in tissue culture medium, for at least about 1 hour, such as at least about 12 hours, 18 hours, 24 hours, 30 hours, 36 hours, 42 hours, 48 hours, 60 hours, 3 days, 4 days, 5 days, 6 days, 7 days, 8 days, 9 days, 10 days, 11 days, 12 days, 13 days, or even at least about 14 days. Incubating may comprise incubating the MILs for about 1 hour to about 30 days, such as about 1 day to about 20 days, about 1 day to about 14 days, about 1 day to about 12 days, or about 2 days to about 12 days.

In some embodiments, the cell is transfected or infected with a nucleic acid molecule encoding a CAR described herein after being placed in a normoxic environment or before it is placed in a normoxic environment.

In some embodiments, the MILs are obtained by extracting a bone marrow sample from a subject and culturing/incubating the cells as described herein. In some embodiments, the bone marrow sample is centrifuged to remove red blood cells. In some embodiments, the bone marrow sample is not subject to, or obtained by, apheresis. In some embodiments, the bone marrow sample does not comprise peripheral blood lymphocytes ("PBL") or the bone marrow sample is substantially free of PBLs. These methods select for cells that are not the same as what have become to be known as TILs. Thus, a MIL is not a TIL.

In some embodiments, the cells can then be plated in a plate, flask, or bag. In some embodiments, hypoxic conditions can be achieved by flushing either the hypoxic chamber or cell culture bag for 3 minutes with a 95% Nitrogen and 5% $CO_2$ gas mixture. This can lead to, for example, 1-2% or less $O_2$ gas in the receptacle. Cells can be then cultured as described herein or as in the examples of WO2016037054, which is hereby incorporated by reference.

In some embodiments, a hypoxic MIL comprising a CAR as described herein is provided. In some embodiments, the hypoxic MIL is in an environment of about 0.5% to about 5% oxygen gas. In some embodiments, the hypoxic MIL is in an environment of about 1% to about 2% oxygen gas. In some embodiments, the hypoxic MTh is in an environment of about 1% to about 3% oxygen gas. In some embodiments, the hypoxic MIL is in an environment of about 1% to about 4% oxygen gas. A hypoxic MIL is a MIL that has been incubated in a hypoxic environment, such as those described herein, for a period of time, such as those described herein. As described herein, the hypoxic MIL can also be activated in the presence of anti-CD3/anti-CD28 beads or other similar activating reagents. Thus, a hypoxic MIL comprising a CAR can also be an activated-hypoxic MIL.

VII. METHODS OF TREATMENT

In some embodiments a cell (e.g., MIL) expressing a CAR is provided. The cell (or a parent cell) may be transfected with a vector comprising a nucleotide sequence encoding the CAR. The vector may be a lentiviral vector (LV). For example, the LV encodes a CAR that combines an antigen recognition domain of a specific antibody with an intracellular domain of CD3ζ, CD28, 4-1BB, or any combinations thereof. Therefore, in some instances, the transduced MIL can elicit a CAR-mediated T-cell response.

Provided herein are the uses of a CAR to redirect the specificity of a primary MIL to a tumor antigen. Thus, in some embodiments, methods for stimulating a MIL-mediated immune response to a target cell population or tissue in a mammal comprising the step of administering to the subject a MTh that expresses a CAR, wherein the CAR comprises a binding moiety that specifically interacts with a predetermined target, a ζ chain portion comprising for example the intracellular domain of human CD3ζ, and a costimulatory signaling region are provided.

In some embodiments, cellular therapies are provided where MILs are genetically modified to express a CAR and the CAR-MIL is infused to a recipient in need thereof. The infused cell is able to kill tumor cells (or other targets) in the recipient. Unlike antibody therapies, CAR-MILs are able to replicate in vivo resulting in long-term persistence that can lead to sustained tumor control.

In some embodiments, the CAR-MILs can undergo robust in vivo MIL expansion and can persist for an extended amount of time.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In some embodiments, the antigen bind moiety portion of the CAR is designed to treat a particular cancer. For example, the CAR designed to target CD19 can be used to treat cancers and disorders including but are not limited to pre-B ALL (pediatric indication), adult ALL, mantle cell lymphoma, diffuse large B-cell lymphoma, salvage post allogenic bone marrow transplantation, and the like.

In some embodiments, the CAR can be designed to target CD22 to treat diffuse large B-cell lymphoma.

In some embodiments, cancers and disorders include but are not limited to pre-B ALL (pediatric indication), adult ALL, mantle cell lymphoma, diffuse large B-cell lymphoma, salvage post allogenic bone marrow transplantation, and the like can be treated using a combination of CARs that target CD19, CD20, CD22, and ROR1.

In some embodiments, the CAR can be designed to target mesothelin to treat mesothelioma, pancreatic cancer, ovarian cancer, and the like.

In some embodiments, the CAR can be designed to target CD33/IL3Ra to treat acute myelogenous leukemia and the like.

In some embodiments, the CAR can be designed to target c-Met to treat triple negative breast cancer, non-small cell lung cancer, and the like.

In some embodiments, the CAR can be designed to target PSMA to treat prostate cancer and the like.

In some embodiments, the CAR can be designed to target Glycolipid F77 to treat prostate cancer and the like.

In some embodiments, the CAR can be designed to target EGFRvIII to treat gliobastoma and the like.

In some embodiments, the CAR can be designed to target GD-2 to treat neuroblastoma, melanoma, and the like.

In some embodiments, the CAR can be designed to target NY-ESO-1 TCR to treat myeloma, sarcoma, melanoma, and the like.

In some embodiments, the CAR can be designed to target MAGE A3 TCR to treat myeloma, sarcoma, melanoma, and the like.

However, the embodiments should not be construed to be limited to solely to the antigen targets and diseases disclosed herein. Rather, the embodiments should be construed to include any antigenic target that is associated with a disease where a CAR can be used to treat the disease.

The CAR-modified MILs may also serve as a type of vaccine for ex vivo immunization and/or in vivo therapy in a subject, such as a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells. In some embodiments, all of the steps are performed prior to administering the cells into a mammal.

Ex vivo procedures are well known in the art and are discussed more fully below. Briefly, cells are isolated from a mammal (such as a human) and genetically modified (i.e., transduced or transfected in vitro) with a vector expressing a CAR disclosed herein. The CAR-MIL can be administered to a mammalian recipient to provide a therapeutic benefit. The mammalian recipient may be a human and the CAR-MIL can be autologous with respect to the recipient. Alternatively, the cells can be allogeneic, syngeneic or xenogeneic with respect to the recipient.

In addition to using a cell-based vaccine in terms of ex vivo immunization, also provided herein are compositions and methods for in vivo immunization to elicit an immune response directed against an antigen in a patient.

Generally, the cells activated and expanded as described herein may be utilized in the treatment and prevention of diseases that arise in individuals who are immunocompromised. In some embodiments, the CAR-modified MILs are used in the treatment of CCL. In some embodiments, the cells are used in the treatment of patients at risk for developing CCL. Thus, methods are provided for the treatment or prevention of CCL comprising administering to a subject in need thereof, a therapeutically effective amount of the CAR-modified MILs.

The CAR-modified MILs may be administered either alone, or as a pharmaceutical composition in combination with diluents and/or with other components such as IL-2 or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In some embodiments, compositions are formulated for intravenous administration.

Pharmaceutical compositions may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions to be administered can be determined by a physician with consideration of individual differences in age, weight, tumor size, extent of infection or metastasis, and condition of the patient (subject). It can generally be stated that a pharmaceutical composition comprising the MILs described herein may be administered at a dosage of $10^4$ to $10^9$ cells/kg body weight, preferably $10^5$ to $10^6$ cells/kg body weight, including all integer values within those ranges. MIL compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In some embodiments, the MIL compositions are administered to a patient by intradermal or subcutaneous injection. In some embodiments, the MIL compositions are administered by intravenous injection. The compositions of MILs may, for example, be injected directly into a tumor, lymph node, or site of infection.

In some embodiments, cells activated and expanded using the methods described herein, or other methods known in the art where MILs are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In some embodiments, the MILs may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun 5:763-773, 1993). In some embodiments, the cell compositions are administered to a patient in conjunction with (e.g., before, simultaneously or following) bone marrow transplantation, MIL ablative therapy using either chemotherapy agents such as, fludarabine, external-beam radiation therapy (XRT), cyclophosphamide, or antibodies such as OKT3 or CAMPATH. In some embodiments, the cell compositions are administered following B-cell ablative therapy such as agents that react with CD20, e.g., Rituxan. For example, in some embodiments, subjects may undergo standard treatment with high dose chemotherapy followed by peripheral blood stem cell transplantation. In some embodiments, following the transplant, subjects receive an infusion of the expanded immune cells described herein. In some embodiments, expanded cells are administered before or following surgery.

The dosage for treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. In some embodiments, the daily dose is 1 to 10 mg per day although in some instances larger doses of up to 40 mg per day may be used (described in U.S. Pat. No. 6,120,766).

VIII. SUBJECTS

The subject may be any organism that comprises MILs. For example, the subject may be selected from rodents, canines, felines, porcines, ovines, bovines, equines, and primates. The subject may be a mouse or a human.

The subject may have a neoplasm. The neoplasm may be a benign neoplasm, a malignant neoplasm, or a secondary neoplasm. The neoplasm may be cancer. The neoplasm may be a lymphoma or a leukemia, such as chronic lymphocytic leukemia ("CLL") or acute lymphoblastic leukemia ("ALL"). The subject may have a glioblastoma, medulloblastoma, breast cancer, head and neck cancer, kidney cancer, ovarian cancer, Kaposi's sarcoma, acute myelogenous leukemia, and B-lineage malignancies. The subject may have multiple myeloma.

The subject may have acute myelogenous leukemia, adenocarcinoma, osteosarcoma, lymphoblastic leukemia, lymphoma, B-cell lymphomas, B-cell Non-Hodgkin's Lymphoma, a B-lineage lymphoid malignancy, breast cancer, ovarian cancer, cervical cancer, colorectal cancer, epithelial cancer, a glioblastoma, glioma, Hodgkin lymphoma, indolent B-cell lymphoma, leukemia, lymphoma, lung cancer, mantel cell lymphoma, medulloblastoma, melanoma, neuroblastoma, prostate cancer, follicular lymphoma, renal cell carcinoma, rhabdomyosarcoma.

EXAMPLES

The following examples are illustrative, but not limiting, of the methods and compositions described herein. Other suitable modifications and adaptations of the variety of conditions and parameters normally encountered in therapy and that are obvious to those skilled in the art are within the spirit and scope of the embodiments.

Example 1: MIL-CAR is Used to Treat B-Cell Lymphoma

A MIL is obtained from a subject with B-Cell Lymphoma. Briefly, after the marrow sample is obtained from the subject, the cells are incubated under hypoxic conditions in the presence of anti-CD3/anti-CD28 beads and cytokines as described in WO2016037054, which is hereby incorporated by reference. A nucleic acid molecule encoding a CAR, comprising the extracellular domain of CD19, the transmembrane domain of CD19, and the intracellular domains of CD3 and 4-1BB is transfected into the MIL. The cells are then grown under normoxic conditions and allowed to expand. The activated and expanded MILs are administered to the subject with B-Cell Lymphoma. The subject's B-Cell Lymphoma is put into remission. In summary, the embodiments and examples provided herein demonstrate that cells expressing a CAR can be effectively used to treat cancer.

Example 2: MIL-CAR is Used to Treat Multiple Myeloma

A MIL is obtained from a subject with multiple myeloma. Briefly, after the marrow sample is obtained from the subject, the cells are incubated under hypoxic conditions in the presence of anti-CD3/anti-CD28 beads and cytokines as described in WO2016037054, which is hereby incorporated by reference. A nucleic acid molecule encoding a CAR, comprising the extracellular domain of CD38, the transmembrane domain of CD8, and the intracellular domains of CD3ζ and 4-1BB is transfected into the MIL. The cells are then grown under normoxic conditions and allowed to expand. The activated and expanded MILs are administered to the subject with multiple myeloma. The subject's multiple myeloma is put into remission.

Any U.S. patents, U.S. patent application publications, U.S. patent applications, foreign patents, foreign patent applications and non-patent publications, including CAS numbers, referred to in this specification and/or listed in the Application Data Sheet are incorporated herein by reference, in their entirety.

What is claimed is:

1. A marrow infiltrating lymphocyte ("MIL"), comprising a chimeric antigen receptor ("CAR"), wherein:
   the CAR comprises a scFV antigen-binding domain that can bind to an extracellular domain of CD19 or CD38; and
   a transmembrane domain of CD19 or CD8, and an intracellular domain selected from the group consisting of 4-1BB, CD3ζ, and a combination thereof and wherein the MIL is autologous MIL isolated from a cancer patient.

2. The MIL of claim 1, wherein the MIL is CD3+, CD4+, CD8+, or a combination thereof.

3. The MIL of claim 1, wherein the MIL is CD45RO+, CD62L+, or CXCR4+.

4. The MIL of claim 1, wherein the MIL is 4-1BB+.

5. The MIL of claim 1, wherein the MIL is interferon γ+ and/or is CD138+.

6. The MIL of claim 1, wherein the MIL is CD33+.

7. The MIL of claim 1, wherein the MIL is CD34-.

8. A method of inhibiting the growth of a neoplastic cell that expresses CD19 or CD38 in a subject, comprising administering to the subject the CD19 or CD38 binding MIL of claim 1.

* * * * *